United States Patent [19]

Harfenist et al.

[11] Patent Number: 4,623,656
[45] Date of Patent: Nov. 18, 1986

[54] METHOD FOR INHIBITING MONOAMINE OXIDASE-A AND TREATING DEPRESSION BY ADMINISTERING 3-N-METHYL-THIOXANTHEN-9-ONE CARBOXAMIDE 10,10-DIOXIDE

[76] Inventors: Morton Harfenist, Rte. 6, Box 405, Chapel Hill, N.C. 27514; Charles T. Joyner, Rte. 8, Box 183H, Raleigh, N.C. 27612

[21] Appl. No.: 704,744

[22] Filed: Feb. 25, 1985

Related U.S. Application Data

[63] Continuation-in-part of Ser. No. 688,718, Jan. 4, 1985, abandoned.

[30] Foreign Application Priority Data

Jan. 5, 1984 [GB] United Kingdom ................ 8400201

[51] Int. Cl.$^4$ ............................................. A61K 31/39
[52] U.S. Cl. ....................................... 514/437; 549/27
[58] Field of Search ........................... 549/27; 514/437

[56] References Cited

U.S. PATENT DOCUMENTS

| | | | |
|---|---|---|---|
| 3,310,553 | 3/1967 | Bloom et al. | 549/27 |
| 3,642,997 | 2/1972 | Shen et al. | 549/27 |
| 4,177,257 | 12/1979 | Hodson et al. | 549/27 |

FOREIGN PATENT DOCUMENTS 1458185 12/1976 United Kingdom ................ 549/27

OTHER PUBLICATIONS

D. Sheehan, J. Clin. Psychiatry 45:7, (1984), pp. 29–36.

Primary Examiner—Henry R. Jiles
Assistant Examiner—J. G. Mullins
Attorney, Agent, or Firm—Donald Brown

[57] ABSTRACT

3-N-methylcarbamoylthioxanthen-9-one 10,10-dioxide of formula (I)

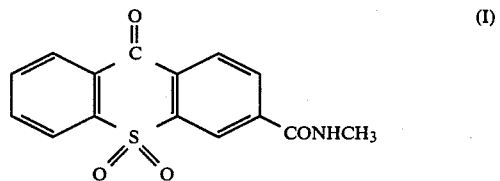

is an inhibitor of monoamine oxidase-A, and is therefore useful in the prophylaxis and treatment of certain mental disorders such as depression.

3 Claims, No Drawings

METHOD FOR INHIBITING MONOAMINE OXIDASE-A AND TREATING DEPRESSION BY ADMINISTERING 3-N-METHYL-THIOXANTHEN-9-ONE CARBOXAMIDE 10,10-DIOXIDE

This application is a continuation-in-part of Application Ser. No. 688,718 filed Jan. 4, 1985 now abandoned.

Monoamine oxidase (MAO) is a brain enzyme believed to be responsible for intraneuronal catalysis of oxidation of biogenic amine neurotransmitters to inactive forms. It is understood to occur as two independent enzymes normally designated MAO-A and MAO-B (White and Glassman, J. Neurochem., 29, 989–997, (1977) and Tipton et al, "Monoamine Oxidase and its Selective Inhibitors", Beckmann and Riederer, Eds., Mod. Probl. Pharmacopsychiat., 19 15–30, Karger, Basel (1983)). MAO inhibition has been found to elevate neurotransmitter concentration in the brain. MAO inhibitors are used therapeutically in the treatment of a wide variety of conditions, especially depression, particularly when characterized by anxiety obsessional neuroses, or appetite disorders. However, many known MAO inhibitors such as phenelzine have an undesirable side effect associated with ingestion of food or drink containing tyramine, for example certain cheeses. When a patient receiving a conventional MAO inhibitor ingests a tyramine containing product, then his blood pressure may be raised, sometimes to a dangerous level. Such patients are therefore instructed to avoid certain foods.

We have now discovered that 3-N-methylcarbamoyl-thioxanthen-9-one 10,10-dioxide, (I) a novel compound, hereinafter also referred to as "Compound I",

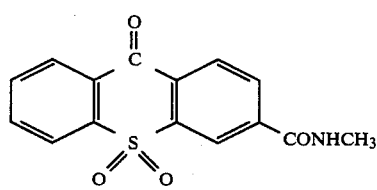

(I)

has antidepressant activity and is unexpectedly superior to the MAO inhibitng type of antidepressants now in clinical use.

No significant hypertensive activity has been observed in test animals which have been given oral antidepressant doses of Compound I prior to orally ingested tyramine.

Compound I may also be named N-methyl-9-oxo-thioxanthene-3-carboxamide 10,10-dioxide.

The present invention further includes a method of inhibiting monoamine oxidase-A (MAO-A) in mammals including humans. This method comprises administration to a mammal which has been identified as being in need of inhibition of monoamine oxidase-A of 3-N-methylcarbamoylthioxanthen-9-one 10,10 dioxide in an amount sufficient to inhibit the MAO-A in the brain.

This invention also includes a method of treatment of depression in a human identified as having depression. This method comprises administration of a therapeutically effective depression treatment amount of 3-N-methylcarbamoylthioxanthen-9-one 10,10-dioxide to a human identified as having depression.

Depression states in which this invention is particularly useful as those defined in the *Diagnostic and Statistical Manual of Mental Disorders*, third edition, (DSM III), American Psychiatric Association, Washington, D.C. (1980), (DSM III, 296.2X to 296.6X and 31.13), including that characterized by anxiety or obsessional neuroses (DSM III, 300.40), or atypical depression (DSM III, 296.70 and 296.82), e.g., accompanied by a personality disorder.

Other therapeutic uses for the compound I include prophylaxis or treatment of obsessive compulsive behavioral states (DSM III, 300.30), anxiety states (DSM III, 300.00, 300.01, 300.02, 300.21, 300.22, 300.23 and 300.29), e.g., which are accompanied in an acute phase by panic attacks with or without phobia (DSM III 300.21), phobia (DSM III 300.23 and 300.29), appetite disorders, e.g., bulimia (DSM III, 307.51) and anorexia (DSM III, 307.10) in humans identified as having such disorders.

Compound I may be administered, for example, by the oral, rectal or parenteral route. In general, the compound may be administered for all the disorders states hereinabove including depression in the dosage range of 1 mg to 100 mg per kg of human bodyweight per day, although the precise dosage will naturally depend on a number of clinical factors, for example, age of the recipient, the condition under treatment, and its severity. For administration of compound I by the oral route, a dosage regime of 5 to 50 mg per kg per day preferably 10 to 40, e.g., about 25 mg per kg per day, may be used. For administration by the parenteral route a dosage regime of 0.2 to 10 mg per kg per day, advantageously 1 to 5 mg per kg per day, e.g., about 2 mg per kg per day is generally preferred.

While it is possible to administer Compound I as the raw compound, it is highly desirable to administer it in the form of a pharmaceutical formulation.

The present invention thus further provides pharmaceutically acceptable formulations comprising as active ingredient, the compound of the invention (as defined above), in association with at least one pharmaceutical carrier or excipient therefor. The pharmaceutical formulations may be adapted for oral, parenteral or rectal administration.

The formulations may conveniently be presented in unit dosage form and may be prepared by any of the methods well known in the art of pharmacy. Such methods include the step of bringing into association the active ingredient with the carrier which may comprise one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid or as an oil-in-water liquid emulsion or a water-in-oil liquid emulsion.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for rectal administration may be presented as a suppository with the usual carriers such as cocoa butter.

Formulations suitable for parenteral administration include aqueous sterile injection solutions which may contain antioxidants, buffers, bacteriostats and solutes which render the formulation isotonic with the blood of the intended recipient; and aqueous and nonaqueous sterile suspensions which may include suspending agents and thickening agents. The formulations may be presented in unitdose or multidose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powder, granules and tablets of the kind previously described.

Preferred unit dosage formulations are those containing a daily dose or unit daily subdose, as hereinabove recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

According to a further feature of the present invention we provide a process for the preparation of the compound of the present invention (as defined above) which comprises:

(a) reacting 3-carboxythioxanthen-9-one 10,10-dioxide with an agent or agents serving to effect conversion of the 3-carboxy substituent thereof to an N-methylcarbamoyl group;

(b) reacting 3-carbamoylthioxanthen-9-one 10,10-dioxide with a methylating agent such as a methyl halide or sulfonate, e.g., methyl iodide; or (c) oxidizing the sulfur atom in the thioxanthene ring structure of 3-N-methylcarbamoyl-9H-thioxanthene, or the corresponding 9-OH analogue and simultaneously or subsequently oxidising the methylene or -CHOH group in the 9-position of the thioxanthene ring structure;

(d) oxidizing the sulfur atom of 3-N-methylcarbamoylthioxanthe-9-one.

In process (a) the reaction may proceed by reaction with a reagent leading to formation of a corresponding activated acid or acid derivative, in the presence of, or followed by reaction with an aminating agent such as methylamine, preferably under aqueous conditions or in a nonhydroxylic solvent. The reagent serving to effect formation of a corresponding activated acid or derivative may be a sulfur oxychloride such as thionyl chloride, a phosphorus halide such as phosphorus tri- or pentachloride, a phosphorus oxyhalide such as the oxychloride, trifluoroacetic anhydride, an alkyl- (eg., ethyl-) chloroformate or any other suitable agent which will be apparent to those skilled in the art. A list of such reagents appears in Methoden der organischen Chemie, Houben-Weyl, 4th Edn., Vol 15, 1, p.29. The reaction may be performed in a suitable solvent such as toluene, desirably in the presence of an appropriate catalyst such as dimethylformamide. Alternatively the reaction may be effected by reaction with an appropriate weak or volatile base such as methylamine, preferably by heating. Such a reaction conveniently may be effected using a stream of methylamine or by use of methylamine in situ in the presence of a dehydrating agent.

In processes (c) and (d), the oxidation of the sulphur atom in the 10-position may be effected by reaction with hydrogen peroxide in acetic acid, with an organic peracid such as meta-chlorobenzoic acid in an inert solvent, e.g., chloroform or dichloromethane, or with an inorganic peracid.

Alternative oxidising agents for use in this stage of the process include ozone and alkali metal permanganates. Where the reaction is performed in an organic solvent, a crown ether is preferably included to ensure solution of the reagent. Other suitable inorganic oxidising agents include alkali metal chromates and dichromates in an unreactive solvent such as acetic acid. Where the step of oxidising the sulphur atom does not simultaneously bring about oxidation of the methylene or —CHOH group in the 9-position, the latter may be effected by admixture with a catalytic amount of a strong base such as an alkali metal hydroxide or alkoxide, e.g., the t-butoxide, thereby promoting the air oxidation.

The starting materials referred to above, 3-carboxy- and 3-carbamoylthioxanthen-9-one 10,10-dioxide may be prepared by processes analogous to those described in the Hodson and Batchelor patent and also in U.S. Pat. Nos. 4,012,499; 4,025,635; 4,103,015; 4,145,350; and 4,177,257. The compound 3-N-methylcarbamoyl-9H-thioxanthene, its salts, and their 9-OH analogues may be prepared by processes analogous to those described in UK patent specification No. 1,458,185.

The following examples illustrate the present invention.

EXAMPLE 1

Preparation of 3-N-methylcarbamoylthioxanthen-9-one 10,10-dioxide

To 345.2 g (1.2 mol) of 3-carboxy-10,10-dioxothioxanthone was added 1.5 Kg $SOCl_2$ and the mixture refluxed overnight. A further 500 g of $SOCl_2$ was added and reflux continued for a further day. Excess $SOCl_2$ was removed under vacuum (water aspirator). The residue was cautiously added with cooling and stirring to 1500 g of cold 70% aq. $NH_2CH_3$ and stirred for 2 days. The precipitate was filtered, washed with aq. $NaHCO_3$ and dried to leave a solid residue, weight 328 g. The procedure was repeated using a further 200 g of acid starting material.

The resultant solids were washed in $NaHCO_3$ solution then filtered and recrystallised from EtOH, DMSO and water. The crystals were filtered, washed with water and dried. The filtrate was diluted with water until cloudy and heated to solution. Further recrystallisation yielded a solid m.p. 223°–225° C. Tlc ($CHCl_3$:acetone/9:1) one spot $R_f$0.49. Analysis: calc. C 59.79, H 3.68, N 4.65; found C 59.74, H 3.71, N 4.62. Structure confirmed by NMR.

EXAMPLE 2

Pharmaceutical Formulations

In the following formulation examples, 'active ingredient' means 3-N-methylcarbamoylthioxanthen-9-one 10,10-dioxide, i.e., compound I.

| A - 100 mg Compression Coated Tablet | | |
|---|---|---|
| | Ingredients | Amount Per Tablet |
| Core | Active Ingredient | 100 mg |
| | Cornstarch | 25 mg |
| | Magnesium Stearate | 2 mg |
| Coating | Coating Lactose | 320 mg |
| | Cornstarch | 50 mg |
| | Gelatin | 6 mg |
| | Magnesium Stearate | 4 mg |

The active ingredient and starch are granulated with water and dried. Magnesium stearate is added to the dried granules. Lactose and starch are granulated with a 10% w/v aqueous solution of gelatin and dried. Magnesium stearate is added to the dried granules. The granulated core is compressed with the granulated coating in a conventional compression molding machine.

| B - 200 mg Capsule | |
|---|---|
| Ingredients | Amount Per Capsule |
| Active Ingredient | 200 mg |
| Lactose | 200 mg |
| Talc | 40 mg |

The active ingredient, lactose and talc are brought into intimate admixture with one another and 440 mg of the resultant mixture is introduced into a size 0 hard gelatin capsule.

| C - 100 mg Capsule | |
|---|---|
| Ingredients | Amount Per Capsule |
| Active Ingredient | 100 mg |
| Lactose | 100 mg |
| Cornstarch | 100 mg |
| Magnesium Stearate | 10 mg |

The ingredients are mixed together until homogeneous and 310 mg of the resulting mixture filled into each hard gelatin capsule.

| D - 500 mg Tablet | |
|---|---|
| Ingredients | Amount Per Tablet |
| Active Ingredient | 500 mg |
| Cornstarch | 100 mg |
| Microcrystalline Cellulose | 75 mg |
| Magnesium Stearate | 5 mg |
| Granulated polyvinylpyrrolidone 10% w/v in 50% w/v aqueous ethanol | 10 mg |

The active ingredient, corn starch and microcrystalline cellulose are mixed together, and granulated with the alcoholic Polyvinylpyrrolidone. The resulting granules are dried, and compressed to produce tablets, each tablet having a weight of approximately 690 mg.

| E - Suppository | |
|---|---|
| Ingredients | Amount Per Suppository |
| Active Ingredient | 200 mg |
| Suppository Base | q.s. 2 g |

The active ingredient in fine powder form is dispersed into a little of the molten Suppository Base at 50° C. The dispersion is incorporated into the bulk of the base at the same temperature, allowed to cool at 42°–45° C., poured into suitable 2 g suppository molds and allowed to set at 15°–20° C. Suppository bases were Massa Esterinum C and Witten H Suppository Compound.

| F - Dispersible Tablet | |
|---|---|
| Ingredients | Amount Per tablet |
| Active Ingredient | 200 mg |
| Corn Starch | 40 mg |
| Primojel (Trade name: sodium starch glycollate (125#m powder)) | 50 mg |
| Dicalcium Phosphate Dihydrate | 50 mg |
| Sodium Carboxymethyl Cellulose | 2 mg |
| Sodium Saccharin | 5 mg |
| Microcrystalline Cellulose | 50 mg |
| Magnesium Stearate | 3 mg |

The active ingredient, half of the corn starch, the Primojel and dicalcium phosphate are mixed together and then granulated with a solution of sodium carboxymethyl cellulose and sodium sacchar in a suitable volume of 50% ethyl alcohol. The granules are dried, the remaining corn starch, the microcrystalline cellulose and the magnesium stearate were blended-in and the resulting mixture compressed into tablets.

EXAMPLE 3

Biological Activity

I. MONOAMINE OXIDASE INHIBITION

A. In Vitro Inhibition

MAO was assayed with [$^3$H] serotonin (0.2 mM, 5 Ci/mol) and [$^{14}$C] $\beta$-phenethylamine (10 $\mu$M, 3 Ci/mol) as substrates in a double-label assay (White and Glassman, J. Neurochem 29:987-97 1977).

For studies of the kinetic mechanism of inhibition, the above method was used, except that a single substrate (serotonin or tyramine) was varied over a 10-fold concentration range that included the $K_m$ concentration. MAO activity was determined in the absence and presence of the compound under test at each substrate concentration in duplicate assays.

Compound (I) produced a potent selective inhibition of MAO-A in mitochondrial extracts of rat or human brain with $I_{50}=0.05$ $\mu$M. This inhibition was competitive vs. the substrates, serotonin or tyramine $K_i=0.016$ $\mu$M with serotonin as substrate.

B. In Vivo Inhibition

To determine MAO inhibition in brains and livers of rats pretreated with reversible inhibitors, it was necessary to use an assay procedure that minimized dilution of the inhibitor. Thus, high concentrations of brain tissue homogenates were incubated for very short incubation times. For brain assays, initial tissue was 3-fold diluted into each assay. Because of the very high MAO activity in liver homogenates, further dilution of tissue was necessary in order to obtain reliable data. In this case, three different homogenate concentrations were assayed, and precent inhibition was extrapolated to zero tissue dilution. Substrate concentrations were not saturating, but were chosen relative to $K_m$ values for serotonin and phenethylamine in order to give an estimate of MAO-A and B, respectively.

Brains from pretreated male Sprague-Dawley rats (sacrificed 3 hours after oral dosing), were homogenized in a buffer consisting of 0.1M potassium phosphate and 5% sucrose (pH 7.4) at a 1:1 tissue wt/buffer volume ratio, using a motorized Teflon/glass homogenizer. MAO-A and B were determined by incubating 100 µl of tissue homogenate with 50 µl of a double-label substrate mixture to give final concentrations of [$^3$H] serotonin, 0.4 mM (5 Ci/mol); and [$^{14}$C] β-phenethylamine, 20 µM (3 Ci/mol). For blank assays 100 µl portions of homogenate were pre-incubated at 37° C. with pargyline (4 mM) before substrate addition. Incubations were at 37° C. for 30 sec. Assay mixtures were then acidified and products extracted as in the above in vitro method (White and Glassman). Liver tissue was homogenized in the above phosphate-sucrose buffer at a 1:5 tissue wt/buffer volume ratio. Portions (5, 10 and 50 µl) of each homogenate were assayed with 50 µl of the above double-label substrate mixture in a total assay volume of 150 µl 0.067M potassium phosphate, pH 7.4. Blank assays included the same amounts of homogenate pre-incubated with 4 mM pargyline for 15 min at 37° C. After addition of substrates, mixtures were incubated at 37° C. for 20 sec, acidified, and products extracted as above. Percent inhibition for each liver homogenate was obtained by plotting % inhibition vs. reciprocal of tissue concentration and extrapolating back to zero dilution.

For Compound I, the following results were obtained at 3 hr after oral dosing.

| Dose | Percentage Inhibition of MAO-A | |
|---|---|---|
| (mg/kg p.o.) | Brain | Liver |
| 12.5 | 37 ± 16 | 79 ± 5 |
| 25 | 49 ± 10 | 94 ± 4 |
| 50 | 78 ± 2 | 92 ± 4 |

There was no significant inhibition of MAO-B in either tissue. In other experiments with the Compound I, for an oral dose of 50 mg/Kg, inhibition was found to maximize within 3-7 hours and to be negligible at 24 hours after dosing, indicating reversibility of the in vivo inhibition.

II. EFFECTS ON BLOOD PRESSURE RESPONSE TO ORAL TYRAMINE

Compound I was tested for effects on the pressor response induced by tyramine in a conscious, unrestrained rat model. The method involves direct measurement of arterial blood pressure from a cannula implanted in the carotid artery and exteriorized through a small incision in the back of the neck. Peak changes in the pressor response following tyramine (p.o.) administration in animals pretreated with the Compound I (p.o.) were compared to changes seen after tyramine in animals pretreated with the MAO inhibitor, phenelzine (p.o.), and control (water-treated) animals.

To compare effects at equipotent doses that are relevant to antidepressant activity, either Compound I or phenelzine was given in a single oral dose that produced approximately 80% inhibition of brain MAO-A by the time of tyramine administration. Under these conditions, MAO-A of liver was inhibited by 90% or more.

Rats treated with vehicle exhibited blood pressure elevations at relatively high doses of tyramine above 27 mg/kg. Phenelzine pretreatment increased the responsiveness to tyramine 3- to 10-fold, while the Compound I did not cause a statistically significant increase in the pressor response to tyramine, except at the high dose comprising 90 mg/kg tyramine.

III. ACTIVITY IN AN ANIMAL MODEL PREDICTIVE OF ANTIDEPRESSANT ACTIVITY

Prevention of Tetrabenazine-Induced Sedation

Charles River CD-1 male mice (18-22 gm) were pretreated orally with various doses of Compound I or the reference standard, phenelzine, 60 min, 3 hr, or 5 hr before injection of tetrabenazine (35 mg/kg i.p.). This dose of tetrabenazine caused 90-100% of treated mice to remain motionless with marked blepharoptosis, even when placed into a novel environment. Thirty minutes after injection of tetrabenazine, each mouse was scored on an arbitrary scale from 6ne to four according to Vernier et al., (in 1st Hahnemann Syomp. on Psychosomatic Medicine, J. H. Nodin and J. H. Moyer Eds., Lea and Febiger, Philadelphia, 1962, pp 683-90) for both depression of exploratory behaviour and presence or absence of blepharoptosis. Ratings were converted to a percent of rating received by mice receiving amitriptyline prior to tetrabenazine administration.

After oral treatment with Compound I (90 minutes) a dose-dependent prevention of tetrabenazine-induced sedation was obtained. The oral ED$_{50}$ for the prevention of tetrabenazine-induced sedation at this time period was 49±10 mg/kg. The ED$_{50}$ values obtained at 3 and 5 hr after treatment with Compound I were essentially the same as those found at 90 min.

We claim:
1. A method of inhibiting monoamine oxidase-A in a mammal identified as being in need of inhibition of monoamine oxidase-A, comprising administration to said mammal of an amount of 3-N-methylcarbamoylthioxanthen-9-one 10,10-dioxide sufficient to inhibit the monoamine oxidase-A.
2. A method of treating depression in a mammal identified as suffering from depression comprising administration to said mammal of an effective depression treatment amount of 3-N-methylcarbamoylthioxanthen-9-one 10,10-dioxide.
3. A method of treatment of depression in a human identified as suffering from depression, comprising administration to said human of a therapeutically effective amount of 3-N-methylcarbamoylthioxanthen-9-one 10,10-dioxide sufficient to treat depression.

* * * * *